(12) United States Patent
Heinisch et al.

(10) Patent No.: US 8,759,573 B2
(45) Date of Patent: Jun. 24, 2014

(54) METHOD FOR PREPARING OPTIONALLY SUBSTITUTED P-HYDROXYMANDELIC COMPOUNDS AND DERIVATIVES THEREOF

(75) Inventors: Bruno Heinisch, Lyons (FR); Pascal Pitiot, Lyons (FR); Jean-Louis Grieneisen, Corbas (FR)

(73) Assignee: Rhodia Operations, Aubervilliers (FR)

( * ) Notice: Subject to any disclaimer, the term of this patent is extended or adjusted under 35 U.S.C. 154(b) by 667 days.

(21) Appl. No.: 12/682,837

(22) PCT Filed: Dec. 9, 2008

(86) PCT No.: PCT/EP2008/067107
§ 371 (c)(1), (2), (4) Date: Sep. 8, 2010

(87) PCT Pub. No.: WO2009/077383
PCT Pub. Date: Jun. 25, 2009

(65) Prior Publication Data
US 2011/0009664 A1     Jan. 13, 2011

(30) Foreign Application Priority Data
Dec. 18, 2007   (FR) ..................... 07 08823

(51) Int. Cl.
*C07C 59/00*      (2006.01)
*C07C 65/21*      (2006.01)
(52) U.S. Cl.
USPC ....................................... 562/470
(58) Field of Classification Search
None
See application file for complete search history.

(56) References Cited

U.S. PATENT DOCUMENTS

| 4,165,341 | A  |   | 8/1979 | Umemura et al. |
|-----------|----|---|--------|----------------|
| 5,138,096 | A  | * | 8/1992 | Schouteeten et al. ......... 562/531 |
| 5,430,183 | A  | * | 7/1995 | Nobel ........................... 562/478 |
| 6,753,441 | B1 |   | 6/2004 | Jouve et al. |

FOREIGN PATENT DOCUMENTS

JP       51-128934       11/1976

OTHER PUBLICATIONS

Mittal et al. (Encyclopedia or Technical Education First Ed., Mittal Publications, vol. 14, 1992, pp. 227, 229-231).*
Le Page (Applied Heterogeneous Catalysis: Design, Manufacture, and Use of Solid Catalysts, Technip Editions, 1987, Ch 8, pp. 241-248).*
http://en.wikipedia.org/wiki/Condensation_reaction.*
Mittal et al. (Encyclopedia or Technical Education First Ed., Mittal Publications, Vo114, 1992, pp. 301-302).*
Don't be baffled by static mixers: how to select and size the correct static mixer; Chemical Engineering; May 1, 2003; http://goliath.ecnext.com/coms2/gi...0199-2806249/Don-t-be-baffled-by.html.
Encyclopedia of Chemical Technology vol. 24, 4$^{th}$ Edition, (1997) pp. 812-825.
Hebert, Bull. Soc. Chim. France, vol. 27, pp. 45-55 (1920).
Smith, et al; Delocalized Chemical Bonding: Advanced Organic Chemistry, 5$^{th}$ Edition, John Wiley sons, 1992, pp. 46-71.

* cited by examiner

*Primary Examiner* — Paul A Zucker
*Assistant Examiner* — Jennifer C Sawyer
(74) *Attorney, Agent, or Firm* — Hunton & Williams LLP

(57) ABSTRACT

The invention relates to a method for preparing optionally substituted P-hydroxymandelic compounds and derivatives thereof. The method for preparing the mandelic compounds of the invention comprises condensing in water, in the presence of an alkaline agent, an aromatic compound bearing at least one hydroxyl group and having a free para position, with glycoxylic acid, wherein said method is characterised in that said reaction is carried out in a piston-flow reactor.

23 Claims, 3 Drawing Sheets

METHOD FOR PREPARING OPTIONALLY SUBSTITUTED P-HYDROXYMANDELIC COMPOUNDS AND DERIVATIVES THEREOF

CROSS-REFERENCE TO RELATED APPLICATIONS

This application is the U.S. National Phase of International Application Number PCT/EP2008/067107 filed on Dec.9, 2008, which claims priority to French Application No. FR 07/08,823, filed Dec.18, 2007, both of which are incorporated by reference herein in their entireties.

FIELD OF THE INVENTION

The present invention relates to a process for preparing optionally substituted p-hydroxymandelic compounds and derivatives thereof.

In the following account of the invention, the term "optionally substituted p-hydroxymandelic compounds" means an aromatic compound at least bearing a group —CHOH—COOH in the para position relative to a hydroxyl group.

The present invention is more particularly directed toward the preparation of p-hydroxymandelic acid, 4-hydroxy-3-methoxymandelic acid and 3-ethoxy-4-hydroxymandelic acid.

BACKGROUND

Vanillin is obtained from natural sources such as lignin or ferulic acid, but a large proportion of vanillin is produced chemically.

Many diverse and varied preparation methods are described in the literature (Kirk-Othmer—Encyclopedia, of Chemical Technology 24, pp. 812-825, 4th edition (1997)).

A standard route of access to vanillin involves a condensation reaction of glyoxylic acid on gaiacol in basic medium, to obtain 4-hydroxy-3-methoxymandelic acid. This product is then oxidized to give vanillin.

The yield for the condensation is limited by the fact that the condensation reaction is not selective and also leads to o-hydroxymandelic acid and to dimandelic acids.

The formation, of dimandelic acids results from a subsequent reaction, namely a second condensation of glyoxylic acid with a mandelic acid.

It is sought to limit the subsequent reactions in order to obtain optimal selectivity.

Continuous processes are usually performed in a cascade of several reactors of perfectly stirred type.

However, multiplying the reactors induces costs both in the implementation and in the exploitation.

SUMMARY OF THE INVENTION

The aim of the invention is to propose a process for preparing mandelic compounds that can overcome one or more of the drawbacks mentioned above, and that can in particular obtain improved selectivity.

The subject of the present invention is thus a process for preparing an optionally substituted p-hydroxymandelic compound and derivatives thereof, comprising the condensation in water, in the presence of an alkaline agent, of an aromatic compound bearing at least one hydroxyl group and whose para position is free, with glyoxylic acid, which is characterized in that the reaction is performed in a piston-flow reactor.

DETAILED DESCRIPTION OF PREFERRED EMBODIMENTS

According to preferred embodiments, the reactor is a tubular reactor or a column reactor.

In the following account of the present invention, the term "tubular reactor" means a reactor of tube shape, and the term "column reactor" means a vertical reactor of circular cross section.

The term "piston flow" defines a unidirectional flow in which, in a plane perpendicular to the flow, all the fluid trickles move at a uniform speed and all the physical magnitudes therein are identical. In such flow, the radial mixing is perfect, whereas there is no axial mixing. In practice, these conditions are considered as being satisfied when the flow is turbulent.

A flow is considered to be turbulent when the Reynolds number is greater than or equal to 2000 and preferentially when it is greater than 5000.

It is recalled that the definition of the Reynolds number is:

$$Re = \frac{\rho \cdot v \cdot d}{\mu}$$

in which:
 $\rho$ is the mass per unit volume of the fluid in kg/m$^3$;
 $v$ is the flow rate in m/s;
 d is the diameter of the reactor in m;
 $\mu$ is the dynamic viscosity in Pa·s.

Figure 3:
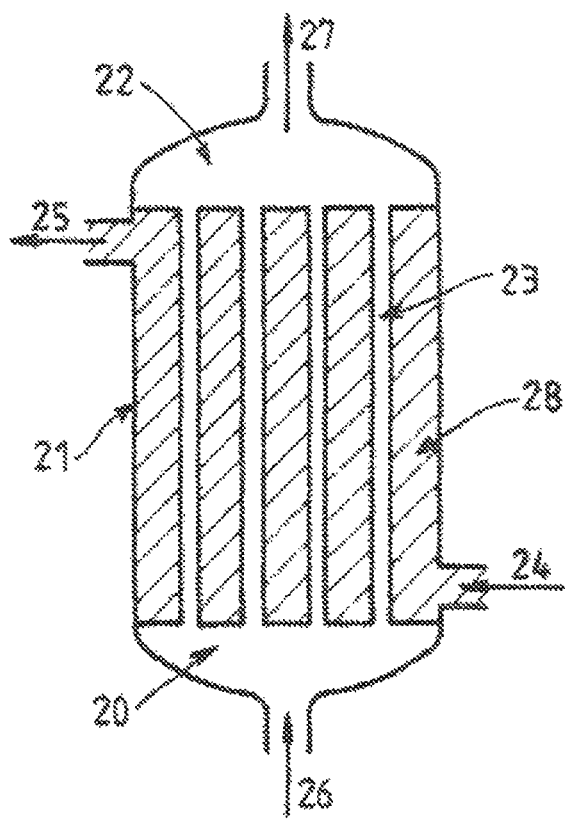

FIG. 3 schematically represents a multitubular reactor comprising tubes bundled together in an array.

In accordance with the process of the invention, it has been found that the use of the process described in a piston-flow tubular reactor makes it possible to obtain improved selectivity. Specifically, good selectivity was obtained on account of limiting subsequent reactions.

The process moreover has the advantage of low bulk and also saving in running and investment costs when compared with a cascade of perfectly stirred reactors, each equipped with means for introducing reagents, for withdrawing products, and also devices for mixing the reagents and for controlling the process parameters.

The process described proposes to prepare p-hydroxymandelic compounds by performing a condensation reaction of an aromatic compound bearing at least one hydroxyl group and of glyoxylic acid in the presence of an alkaline agent and optionally in the presence of a catalyst.

In the account hereinbelow, the term "aromatic compound" means a cyclic compound containing delocalized double bonds as defined in the literature, especially by M. Smith and J. March, Advanced Organic Chemistry, 5th edition, John Wiley & Sons, 1992, pp. 46 et seq.

The process of the invention applies most particularly to an aromatic compound such as phenol, but also to substituted phenols containing at least one unsubstituted position para to the hydroxyl group.

The aromatic nucleus bears at least one hydroxyl group, but it may also bear one or more other substituents. Generally, the term "other substituents" defines less than four substituents per aromatic nucleus.

Any substituent may be present, insofar as it does not interfere with the reaction of the invention.

Thus, the process of the invention is suitable for application to hydroxylated aromatic compounds corresponding to formula (I) below:

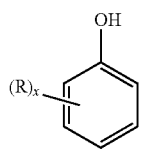
(I)

in said formula:
- at least the position para to the hydroxyl group is free,
- R represents a hydrogen atom or one or more identical or different substituents,
- x, the number of substituents on a ring, is a number less than or equal to 4,
- when x is greater than 1, two groups R placed on two vicinal carbon atoms may form, together with the carbon atoms that bear them, a saturated, unsaturated or aromatic ring containing from 5 to 7 atoms and optionally comprising one or more heteroatoms.

In formula (I), the groups R, which may be identical or different, represent a hydrogen atom, an alkyl, alkenyl, alkoxy, hydroxyalkyl, alkoxyalkyl, cycloalkyl, aryl or arylalkyl group, a hydroxyl group, a nitro group, a halogen atom, a halo or perhaloalkyl group, a formyl group, an acyl group containing from 2 to 6 carbon atoms; a carboxylic group, an amino or amido group optionally substituted with one or two alkyl or phenyl groups. It should be noted that the carboxylic group may be preferably salified with an alkali metal (sodium or potassium) or esterified, for example with an alkyl or phenyl group.

In formula (I), when x is greater than 1, two groups R placed on two vicinal carbon atoms may be linked together via an alkylene, alkenylene or alkenylidene group containing from 3 to 5 carbon atoms, to form a saturated, unsaturated or aromatic ring containing from 5 to 7 atoms: one or more (preferably 2 or 3) carbon atoms possibly being replaced with a heteroatom, preferably oxygen.

In the context of the invention, the term "alkyl" means a linear or branched hydrocarbon-based chain containing from 1 to 15 carbon atoms and preferably 1 or 2 to 10 carbon atoms.

The term "alkoxy" means a group alkyl-O— in which the term alkyl has the meaning given above. Preferred examples of alkoxy groups are methoxy or ethoxy groups.

The term "alkenyl" means a linear or branched hydrocarbon-based group containing from 2 to 15 carbon atoms, comprising one or more double bonds, preferably 1 to 2 double bonds.

The term "cycloalkyl" means a cyclic hydrocarbon-based group comprising from 3 to 8 carbon atoms, preferably a cyclopentyl or cyclohexyl group.

The term "aryl" means a monocyclic or polycyclic aromatic group, preferably a monocyclic or bicyclic group containing from 6 to 12 carbon atoms, preferably phenyl or naphthyl.

The term "arylalkyl" means a linear or branched hydrocarbon-based group bearing a monocyclic aromatic ring and containing from 7 to 12 carbon atoms, preferably benzyl.

The term "halo or perhaloalkyl" means one of the following groups: —CX$_3$, —[CX$_2$]$_p$—CX$_3$ or —C$_p$H$_a$F$_b$ in which said groups X represents a halogen atom, preferably a chlorine or fluorine atom; p represents a number ranging from 1 to 10, b a number ranging from 3 to 21 and a+b=2p+1.

In the case where x is greater than 1, two groups R placed on two vicinal carbon atoms may be linked together via an alkylene, alkenylene or alkenylidene group to form a saturated, unsaturated or aromatic ring containing from 5 to 7 atoms thus forming a bicycle. Examples of preferred bicyclic skeletons are the following:

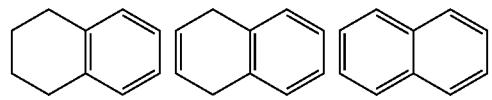

The compounds that are particularly suitable for use in the process of the invention correspond to formula (I) in which R, which may be identical or different, represent:
- a hydrogen atom,
- a hydroxyl group,
- a linear or branched alkyl group containing from 1 to 6 carbon atoms and preferably from 1 to 4 carbon atoms, such as methyl, ethyl, n-propyl, isopropyl, n-butyl, isobutyl, sec-butyl or tert-butyl,
- a linear or branched alkenyl group containing from 2 to 6 carbon atoms and preferably from 2 to 4 carbon atoms, such as vinyl or allyl,
- a linear or branched alkoxy group containing from 1 to 6 carbon atoms and preferably from 1 to 4 carbon atoms, such as methoxy, ethoxy, n-propoxy, isopropoxy, n-butoxy, isobutoxy, sec-butoxy or tert-butoxy groups,
- a phenyl group,
- a halogen atom, preferably a fluorine, chlorine or bromine atom.

As regards the definition of x, x is advantageously equal to 0, 1 or 2 and more preferentially equal to 1.

The invention preferentially applies to compounds corresponding to formula (I) in which R represents a hydrogen atom or an alkyl group containing from 1 to 4 carbon atoms and x is equal to 1.

As illustrations of compounds corresponding to formula (I), mention may be made of:
- those corresponding to formula (I) in which x is equal to 0, such as:
  phenol,
- those corresponding to formula (I) in which x is equal to 1, such as:
  pyrocatechin
  resorcinol
  o-cresol
  m-cresol
  2-ethylphenol
  3-ethylphenol
  2-propylphenol
  2-sec-butylphenol
  2-tert-butylphenol
  3-tert-butylphenol
  2-methoxyphenol (gaiacol)
  3-methoxyphenol
  2-ethoxyphenol (guetol)
  2-isopropoxyphenol
  salicylaldehyde
  methyl salicylate
  2-chlorophenol
  3-chlorophenol
  3-nitrophenol those corresponding to formula (I) in which x is equal to 2, such as:
2,3-dimethylphenol
2,5-dimethylphenol
3,5-dimethylphenol
2-hydroxy-5-acetamidobenzaldehyde
2-hydroxy-5-ethamidobenzaldehyde
2,3-dichlorophenol
2,5-dichlorophenol
3,5-dichlorophenol
pyrogallol
those corresponding to formula (I) in which x is equal to 3, such as:
2,3,5-trimethylphenol
3,5-di-tert-butylphenol
2,3,5-trichlorophenol
those corresponding to formula (I) containing a naphthalene group, such as;
1-naphthol
2-naphthol
1,2-dihydroxynaphthalene
1,5-dihydroxynaphthalene
2,3-dihydroxynaphthalene
2,6-dihydroxynaphthalene
2,7-dihydroxynaphthalene
6-bromo-2-naphthol
those corresponding to formula (I) containing a sequence of benzene nuclei:
2-phenoxyphenol
3-phenoxyphenol Among the abovementioned listed compounds, aromatic compounds bearing at least one hydroxyl group that are preferentially used are: phenol, o-cresol, m-cresol, 3-ethylphenol, 2-tert-butylphenol, gaiacol, guetol.

The compounds to which the process of the invention preferentially applies are gaiacol and guetol.

In accordance with the process of the invention, the condensation of the hydroxylated aromatic compound and of the glyoxylic acid is performed in the liquid phase, in the presence of an alkaline agent.

As alkaline agents, use is preferably made of an alkali metal hydroxide, which may especially be sodium or potassium hydroxide. For economic reasons, sodium hydroxide is preferentially chosen.

The presence of the base leads to salification of the hydroxylated aromatic compound, on the one hand, and of the carboxylic function, on the other hand.

The alkali metal hydroxide solution used has a concentration generally of between 10% and 50% by weight.

The amount of alkali metal hydroxide introduced into the reaction medium takes into account the amount necessary to salify the hydroxyl function of the hydroxylated aromatic compound and the carboxylic function of the glyoxylic acid.

Generally, the amount of alkali metal hydroxide ranges between 80% and 120% of the stoichiometric amount.

The glyoxylic acid may be used as an aqueous solution at a concentration ranging from, for example, between 15% and 70% by weight. Use is preferably made of commercial solutions whose concentration is about 50% by weight.

The glyoxylic acid is reacted with the hydroxylated aromatic compound. The mole ratio between the hydroxylated aromatic compound and the glyoxylic acid ranges between 1.0 and 4.0.

The concentration of the hydroxylated aromatic compound is preferably between 0.5 and 1.5 mol/liter and more particularly about 1 mol/liter.

One possible variant consists in performing the reaction in the presence of a catalyst of dicarboxylic acid type, preferably oxalic acid, as described in WO 99/55853.

The amount of catalyst used, expressed as the ratio between the number of moles of catalysts and the number of moles of glyoxylic acid, is advantageously chosen between 0.5% and 2.5% and preferably between 1% and 2%.

The reaction temperature is advantageously chosen between 20° C. and 90° C. and preferably between 30° C. and 40° C.

The reaction is performed at atmospheric pressure, but under a controlled atmosphere of inert gases, preferably nitrogen or optionally rare gases, in particular argon. Nitrogen is preferentially chosen.

Preferably, the hydroxylated aromatic compound and the base are mixed together beforehand. This variant allows better control of the temperature during the exothermic salification reaction of the glyoxylic acid.

Thus, according to one preferred embodiment of the process, the hydroxylated aromatic compound is first placed in contact with the alkali metal hydroxide in aqueous solution.

The resulting solution is then placed in contact with the glyoxylic acid and the mixture obtained is then introduced into the piston-flow reactor.

The mixture obtained has a viscosity at 20° C. of between 1.5 and 3 mPa·s.

The rate of introduction of said mixture ranges between 0.010 and 20 m³/h.

The residence time in the reactor is preferably between 10 minutes and 2 hours.

At the end of the reaction, the p-hydroxymandelic compound obtained is separated from the reaction mixture in salified form according to the standard separation techniques, especially by crystallization or by extraction using a suitable organic solvent.

The process of the invention leads to the production of optionally substituted p-hydroxymandelic compounds, which may be represented by formula (II) below:

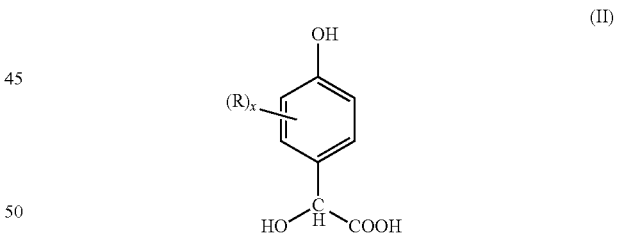

in said formula (II), R and x having the meaning given in formula (I).

These products are particularly valuable since they are intermediates for, inter alia, obtaining, via reduction, hydroxyarylacetic acids or, via oxidation, hydroxyarylglyoxylic acids (=hydroxyaryl-α-oxoacetic acids) or hydroxyaromatic aldehydes.

One preferred application of the invention is the preparation of hydroxyaromatic aldehydes, via oxidation of the compounds of formula (II) obtained according to the invention.

The reaction mixture obtained previously may be used without further processing. However, it is preferable to recover the unreacted hydroxylated aromatic compound.

To this end, the work-ups described in the prior art, especially in FR-A-2 379 501, may be used.

This consists in adding a mineral acid, for example hydrochloric acid or sulfuric acid, so as to adjust the pH to between 5 and 7 and then in extracting the unreacted hydroxylated aromatic compound into an organic solvent, especially ether, toluene, etc.

After extraction, the aqueous and organic phases are separated.

The aqueous phase comprises the p-hydroxymandelic compound (II), which will then be oxidized.

The oxidation may be performed according to the techniques described in the literature. Thus, reference may be made to P. Hebert [Bull. Soc. Chim. France, 27, pp. 45-55 (1920)] and to Nagai Shigeki et al.: [JP-A 76/128 934]. The oxidation is generally performed with oxygen or air under pressure, in basic medium and in the presence of a suitable catalyst, for instance chromium, cobalt, copper, vanadium or osmium derivatives.

Thus, the invention readily affords access to 4-hydroxybenzaldehyde and to vanillin and analogs thereof, for example 3-ethylvanillin, or 3-isopropylvanillin, by oxidation, respectively, of p-hydroxymandelic acid and of 4-hydroxy-3-methoxymandelic acid, 3-ethoxy-4-hydroxymandelic acid and 4-hydroxy-3-isopropoxymandelic acid.

The reactor in which the process according to the invention is performed is a piston-flow reactor.

Usually, the reactor will have a length/diameter ratio of greater than 3. It may especially be a tubular reactor with a length/diameter ratio of between 4 and 30 and in particular between 5 and 10.

Advantageously, the tubular reactor is formed so as to have little bulk, for example when it is bent.

The material of the reactor is not particularly limited. It will be chosen so as to be inert under the reaction conditions. Generally, a reactor made of stainless steel will be chosen.

Tubular reactors are generally arranged horizontally. However, in order to adapt to spatial constraints, it may also be envisioned to provide a reactor arranged vertically or inclined. Preferably, the reactor is arranged vertically.

In the case of an inclined or vertical reactor, it is preferred to feed the reactor from the bottom, so as to facilitate the degassing operation.

Advantageously, one or more perforated plates are placed in proximity to the reagent inlet so as to ensure good homogeneity of the fluids in this section of the reactor.

Advantageously, the tubular reactor is in the form of a column. It is equipped with pipes for introducing reagents and for removing the reaction mixture. The reagents are fed in by standard means, for instance a pump and more particularly a centrifugal pump or a positive displacement pump.

In principle, it is preferred to work in the liquid phase only, in the absence of a gaseous phase.

The tubular reactor may be equipped with packing.

The presence of packing in the reactor creates turbulences that ensure homogeneity of the reaction mixture throughout the section of the reactor. The packing thus makes it possible to maintain the piston-flow nature, even for low flow rates, for example of mm/s order.

The packing material is not critical, provided that it is chemically inert with respect to the reaction mixture under the reaction conditions. Generally, it is a case of materials such as glass, metal, especially stainless steel, carbon, polymer or ceramic.

Different types of packing may be envisaged.

It may be a case of bulk packing, which consists of small objects, for example in the form of rings, plates, balls or hollow cylinders, with which all or part of the reactor is filled.

Preferably, the packing is arranged in the reactor close to the reagent inlet.

In the case of a reactor arranged vertically, the packing is preferably arranged throughout the height of the reactor. It is then necessary to provide a suitable support, for example in the form of braces, in order to keep the packing in place.

Packing of the static mixer type, composed of mixing elements comprising guide blades set at precise angles and arranged in a complex manner, is particularly preferred. This type of packing is sold, for example, by the company Sulzer under the names SMV and SMX.

For the description of these packings, reference may be made to the article "Don't Be Baffled By Static Mixers" published in Chemical Engineering, May 2003.

From a practical viewpoint, a linear tube without packing, which is folded on itself and arranged horizontally or vertically when the Reynolds number is greater than 2000, and preferentially when it is greater than 5000, is chosen.

When the Reynolds number is less than 2000, it is preferred to use a reactor with packing.

It should be noted that it is possible, when the reactor is a tube folded on itself, to equip it partially with packing. After each bend of the tube, a section of packing of an equivalent length is introduced, for example of 3 to 6 times the diameter of the tube, over all or part of the linear length of the tube located between two successive bends.

The attached figures illustrate the type of apparatus that may be used for performing the process of the invention.

Figure 1:
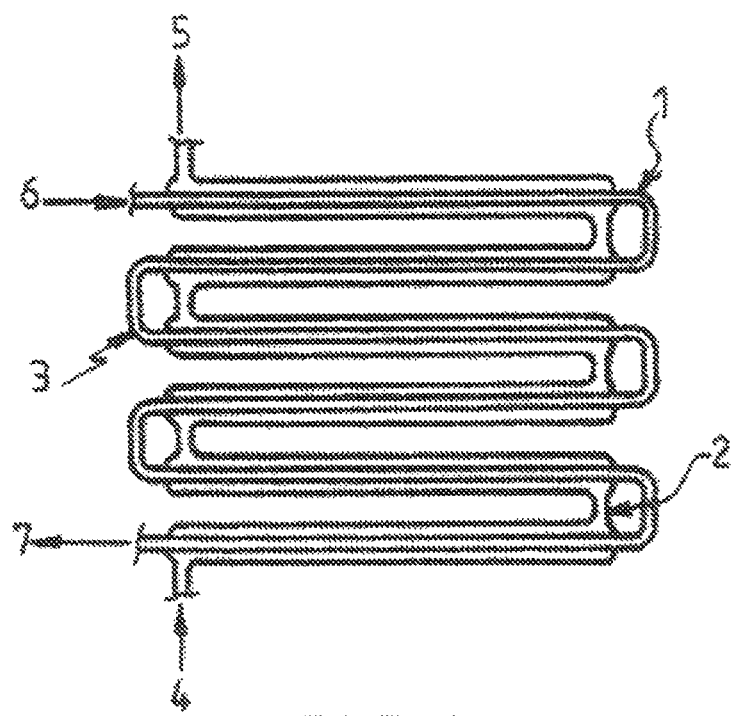
FIG. 1 is a schematic representation of a tubular reactor formed from concentric tubes.

FIG. 1 represents a tubular reactor formed from concentric tubes.

Thus, the reactor is formed from a tube (1) inside which circulate the mixed reagents that enter at (6) and the products that leave at (7).

Heat exchange is ensured by a heat-exchange fluid, circulating in a jacket (2), which enters at (4) and leaves at (5). It is generally water or a suitable organic solvent, for instance an aromatic ether such as diphenyl ether and/or benzyl ether, a paraffinic and/or naphthenic oil, petroleum distillation residues etc.

The tube may contain packing sections after each bend (3).

Figure 2:
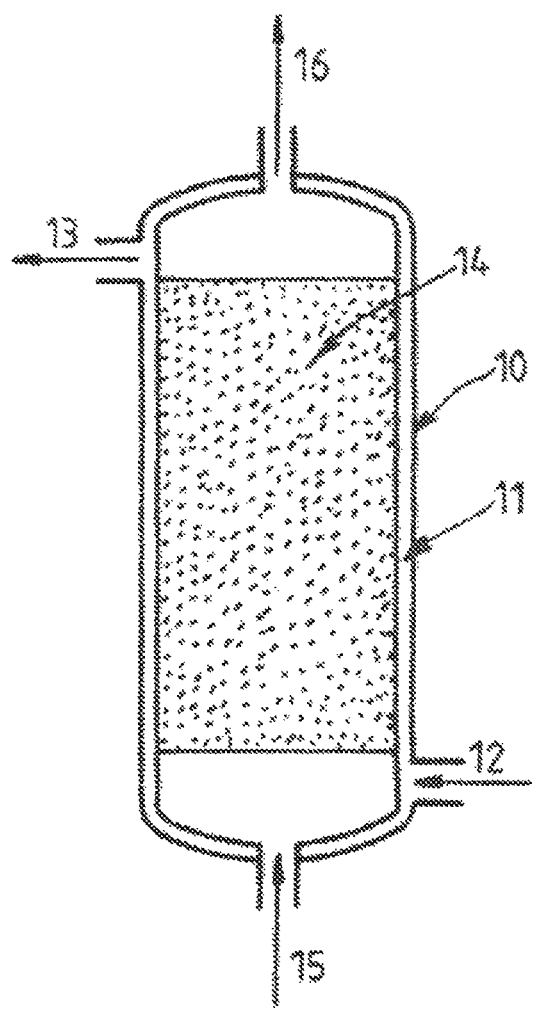
FIG. 2 is a schematic representation of a reactor of column shape.

FIG. 2 represents a reactor in the form of a column (10) equipped with a jacket (11) or any equivalent means, in which circulates a heat-exchange fluid that enters at (12) and leaves at (13).

The column is equipped with packing (14).

The reagents are introduced at (15) and the products leave at (16).

It should be noted that the invention does not exclude the case in which the tubular reactor represented by FIG. 3 is of the vertical multitubular calender exchanger type.

It comprises a reagent introduction zone (20), a central zone (21) and a reagent outlet zone (22). The central zone comprises an array of parallel tubes (23); each tube comprising an inlet opening into the inlet zone and an outlet opening into the outlet zone.

The heat-exchange fluid entering at (24) and leaving at (25) circulates in the calender (28) around the tubes.

The reagents are introduced at (26) and the products leave at (27).

The tubes may or may not be equipped with packing.

The apparatus proposed is particularly useful for the described process since it makes it possible to maintain piston flow for a reaction that requires a long residence time, with low flow rates.

Moreover, it makes it possible to limit the subsequent reactions leading to undesired secondary compounds.

The invention will be explained in greater detail by means of the example below of one preferred embodiment of the invention, which is given without any implied limitation.

EXAMPLES

Unless otherwise mentioned, the percentages indicated are expressed on a weight basis.

In the examples, the degree of conversion, the yield and the selectivity obtained are defined.

The degree of conversion (TT) corresponds to the ratio between the number of moles of reagents (glyoxylic acid) converted to the number of moles of reagent (glyoxylic acid) used.

The selectivity (RT) corresponds to the ratio between the number of moles of product formed (4-hydroxy-3-methoxymandelic acid) to the number of modes of reagent (glyoxylic acid) transformed.

Example 1

The following are fed into a 6 liter reactor equipped with a jacket, a pH electrode, a temperature probe, a condenser, an inert gas inlet and mechanical stirring:
41 kg/h of distilled water,
8.9 kg/h of an aqueous sodium hydroxide solution at 30% by weight,
5.48 kg/h of gaiacol,
3.85 kg/h of an aqueous glyoxylic acid solution at 50% by weight.

This solution is then fed at a flow rate of 58 l/h into a tubular reactor as illustrated by FIG. 2, with a volume of about 15 liters (2 m long and 100 mm in diameter), packed with Sulzer SMX packing.

The temperature of the piston reactor is maintained at 38° C.

Under these conditions, the residence time in the reactor is 16 minutes and the Reynolds number is 140.

On leaving the tubular reactor, the reaction products are assayed by high performance liquid chromatography.

The results obtained are collated in the table below.

No fouling of the reactor is observed, even after several months.

Example 2 (Comparative Example)

Example 1 is repeated, with the exception that the reaction mixture from the first reactor is not introduced into a tubular reactor, but into a cascade of two reactors of perfectly stirred type equipped with an impeller stirrer with 4 inclined paddles, each reactor having a volume of 10 liters.

On leaving the last reactor, the reaction products are assayed by high performance liquid chromatography.

The results are collated in the table below.

TABLE (I)

| Ref. Ex. | Conversion | 4-Hydroxy-3-methoxy-mandelic acid | 2-Hydroxy-3-methoxy-mandelic acid | 2-Hydroxy-3-methoxy-1,5-dimandelic acid |
|---|---|---|---|---|
| 1 | TT = 72.2% | RT = 81.9% | RT = 6.1% | RT = 11.1% |
| 2 | TT = 71.9% | RT = 79.3% | RT = 5.8% | RT = 14.7% |

It is found that for an equivalent degree of conversion, the selectivity toward desired product, 4-hydroxy-3-methoxymandelic acid, is higher for a tubular reactor than for a cascade of reactors of perfectly stirred type.

The use of a tubular reactor comprising packing thus makes it possible to increase the selectivity of the process for preparing p-hydroxymandelic compounds such as 4-hydroxy-3-methoxymandelic acid.

The invention claimed is:

1. A process for preparing an optionally substituted p-hydroxymandelic compound or a derivative thereof, comprising:
reacting an aromatic compound with glyoxylic acid in a piston-flow reactor in the presence of water and an alkaline agent,
wherein said aromatic compound comprises at least one hydroxyl group and an unsubstituted para position.

2. The process of claim 1, wherein the reactor does not comprise any packing when the flow in the reactor has a Reynolds number greater than or equal to 2000.

3. The process of claim 2, wherein the reactor does not comprise any packing when the flow in the reactor has a Reynolds number greater than or equal to 5000.

4. The process of claim 1, wherein the reactor comprises packing when the flow in the reactor has a Reynolds number of less than 2000.

5. The process of claim 1, wherein the reactor has a length/diameter ratio ranging from 4 to 30.

6. The process of claim 5, wherein the reactor has a length/diameter ratio ranging from 5 to 10.

7. The process of claim 1, wherein the reactor comprises a tubular reactor comprising concentric tubes, a column-shaped reactor, or a tubular reactor comprising tubes bundled together in an array.

8. The process of claim 7, wherein the reactor is a column reactor.

9. The process of claim 4, wherein said packing comprises static mixer packing.

10. The process of claim 4, wherein the packing comprises mixing elements comprising guide blades set at angles.

11. The process of claim 1, wherein the hydroxylated aromatic compound comprises a compound of formula (I):

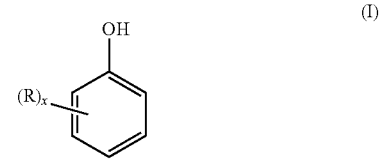

wherein:
at least the position para to the hydroxyl group is free,
R represents a hydrogen atom or one or more identical or different substituents, and
X is less than or equal to 4.

12. The process of claim 11, wherein said compound comprises a saturated, unsaturated or aromatic ring comprising from 5 to 7 atoms including R groups and vicinal carbon atoms to which said R groups are attached.

13. The process of claim 12, wherein said aromatic ring comprises one or more heteroatoms.

14. The process of claim 11, wherein said R represents a hydrogen atom; an alkyl, alkenyl, alkoxy, hydroxyalkyl, alkoxyalkyl, cycloalkyl, aryl or arylalkyl group; a hydroxyl group; a nitro group; a halogen atom; a halo or perhaloalkyl group; a formyl group; an acyl group comprising from 2 to 6 carbon atoms; an optionally salified or esterified carboxylic group; an amino or amido group optionally substituted with an alkyl or phenyl group.

15. The process of claim 11, wherein the hydroxylated aromatic compound comprises phenol, o-cresol, m-cresol, 3-ethylphenol, 2-tert butylphenol, gaiacol or guetol.

16. The process of claim 1, wherein the mole ratio of the hydroxylated aromatic compound to the glyoxylic acid ranges from 1.0 to 4.0.

17. The process of claim 16, wherein the viscosity of the mixture at 20° C. ranges from 1.5 to 3 mPa.

18. The process of claim 1, wherein the reaction temperature ranges from 20° C. to 90° C.

19. The process of claim 18, wherein the reaction temperature ranges from 30° C. to 40° C.

20. A process for preparing a 4-hydroxyaromatic aldehyde comprising:

preparing an optionally substituted p-hydroxymandelic compound by reacting an aromatic compound with glyoxylic acid in a piston-flow reactor in the presence of water and an alkaline agent, wherein said aromatic compound comprises at least one hydroxyl group and an unsubstituted para position, and oxidizing said p-hydroxymandelic compound to yield a 4-hydroxyaromatic aldehyde.

21. The process of claim 20, wherein said oxidation comprises oxidizing 4-hydroxy-3-methoxymandelic acid to vanillin.

22. The process of claim 20, wherein said oxidation comprises oxidizing 3-ethoxy-4-hydroxymandelic acid to ethylvanillin.

23. The process of claim 10, wherein the packing comprises mixing elements comprising guide blades set at precise angles and arranged in a complex manner and sold by the Sulzer company under the names SMV or SMx.

* * * * *